United States Patent [19]

Allocca

[11] 4,204,547
[45] May 27, 1980

[54] METHOD AND APPARATUS FOR NONINVASIVE MONITORING OF INTRACRANIAL PRESSURE

[76] Inventor: John A. Allocca, 2439 Young Ave., Bronx, N.Y. 10469

[21] Appl. No.: 959,458

[22] Filed: Nov. 13, 1978

[51] Int. Cl.² .............................................. A61B 5/05
[52] U.S. Cl. .................................................. 128/748
[58] Field of Search ............... 128/748, 677, 679, 680, 128/668, 692, 630

[56] References Cited

U.S. PATENT DOCUMENTS

| | | | |
|---|---|---|---|
| 3,686,958 | 8/1972 | Porter et al. | 128/748 X |
| 3,757,770 | 9/1973 | Brayshaw et al. | 128/748 |
| 3,877,137 | 4/1975 | Hakim et al. | 128/748 X |
| 3,977,391 | 8/1976 | Fleischmann | 128/748 |
| 4,003,141 | 1/1977 | LeRoy | 128/748 X |
| 4,062,354 | 12/1977 | Taylor et al. | 128/748 X |

*Primary Examiner*—Kyle L. Howell
*Attorney, Agent, or Firm*—Darby & Darby

[57] ABSTRACT

A method and apparatus is disclosed for noninvasive monitoring of the intracranial pressure of mammals. The method preferably consists of occluding the jugular vein at a selected location so as to interrupt the flow of blood temporarily and then determining the rate of change of blood flow within the jugular vein upstream of such location over a predetermined period of time following its occlusion. Means controlled by the operation of a computer may be utilized for automatically occluding the jugular and for inducing detectable electrical signals representative of the flow of blood within the jugular.

21 Claims, 7 Drawing Figures

METHOD AND APPARATUS FOR NONINVASIVE MONITORING OF INTRACRANIAL PRESSURE

BACKGROUND OF THE INVENTION

The invention relates to pressure monitoring devices and techniques, and in particular to a method and apparatus for monitoring the intracranial pressure of the cerebrospinal fluid of mammals without the necessity for surgical or other implantation within the cisterna magna, the lateral cerebral ventricles or the lumbar subarachnoid space of instruments such as needles, catheters and the like. The present invention also enables the monitoring of intracranial pressure without the implantation of sensors, meters, capsules or other transducer type devices within or beneath the surface of the skull.

The ability to monitor the intracranial pressure of an injured or diseased patient has long been of significant diagnostic and postoperative importance in the medical profession, particularly with respect to patients suffering diseases known or suspected of having an affect upon the pressure of the subarachnoidal fluid adjacent the brain.

For example, intracranial pressure monitoring is particularly desirable for hydrocephalic individuals, for individuals who have undergone neurosurgery, and even for those subject to or suspected of experiencing brain swelling, edema, obstruction of cerebrospinal fluid passages, tumors, hemorrhages, infections and the like. Any of these situations can result in sufficient interference with the normal functioning of the regulatory system for controlling pressure of the cerebrospinal fluid (i.e., the rate of cerebrospinal fluid formation and the resistance to absorption through the arachnoidal villi), to increase the chances that intracranial pressure will rise to dangerous levels.

One known technique for measuring the pressure of the cerebrospinal fluid requires the subject to lie precisely horizontally on its side in order to equalize the pressures in the spinal column and the cranial vault. A hollow needle is then inserted into the lumbar spinal canal below the lower end of the cord, and is connected to a glass tube. The spinal fluid passes through the needle out of the spinal canal and rises in the tube to a level corresponding to its internal pressure. Suitable calibration of the tube enables a convenient measure of the fluid pressure, preferably in mmHg.

This technique however is not favored by the medical profession because of the likelihood that in the event of relatively high cerebrospinal fluid pressures, dangerously excessive fluid losses are likely (and have been known) to occur. Moreover, since the cerebrospinal fluid does not clot, additional fluid losses will occur until the punctured dura heals, generally over a period of about one week. In addition, the invasive use of a hollow needle generates considerable patient discomfort and involves a persistent danger of infection. A further disadvantage of this technique, as well as a related technique involving the introduction of a catheter into the ventricular spaces of the brain, is that it is not suitable for monitoring intracranial pressure over prolonged periods of time.

Accordingly, a variety of techniques for measuring intracranial pressure have evolved which avoid the penetration of the dura mater membrane enclosing the central nervous system. These prior methods have commonly involved implantation within the head of the patient of a pressure transducer having wires or tubes which pass outwardly through the scalp and skull for connection to a recording device.

For example, in U.S. Pat. No. 3,877,137 there is disclosed an hydraulic pressure sensor in the form of a compressible bulb or bladder filled with displaceable fluid and adapted for implantation between the skull and the brain of a patient. A pressure sensor which generates optical signals has been suggested (U.S. Pat. No. 3,686,958) for placement within the skull and which is connected to a suitable external interpretive device by way of optical fibers.

In addition, various pressure sensors (U.S. Pat. Nos. 3,757,770 and 4,062,354) have been devised which transmit electrical signals or radiate representative electromagnetic energy to an external receiving or recording apparatus. For example, U.S. Pat. No. 4,003,141 discloses a pressure sensor to be mounted within the skull and which is connected electrically to an external recording mechanism, thereby subjecting the patient to the attendant hazards of electrical shock. Other pressure sensors operating for example on the basis of a discrete mass of radioactive material (U.S. Pat. No. 3,977,391) have also been proposed heretofore. The high medical risk attendant to the use of such a device is self-evident.

Each of these prior devices and techniques has suffered from the disadvantage of requiring placement of the transducer within the cranium of the patient. Implantation and subsequent removal of the pressure transducer exposes the patient to certain surgical risks including a persistent risk of infection. Moreover, these prior systems require periodic adjustment to compensate for changes in the position of a patient and, in some cases, are known to have a tendency to cause leakage or blockage within the skull and therefore affect the measurements being derived.

The result has been a general reluctance on the part of physicians to make use of this diagnostic tool except under the most severe circumstances so that many patients suffering head injuries, for example, have not had the benefit of intracranial pressure monitoring. A dangerous rise in intracranial pressure (which may result, for example, from a small internal hemorrhage) has therefore often gone undiagnosed until clinical symptoms have developed. At this point, it is often too late to provide effective remedial aid (such as through the use of appropriate drugs) short of drastic surgical intervention.

These and other disadvantages of the prior techniques and systems for measuring intracranial pressure have been obviated by the present invention which provides a completely noninvasive apparatus and technique for deriving information relative to the intracranial pressure. The present technique is based essentially upon the heretofore unrealized relationship between the presure of blood in the jugular vein outside of the head and the pressure exerted by the cerebrospinal fluid within the dura membrane of the head. It has been discovered that the intracranial pressure has a detectable effect upon the pressure of blood within the network of vessels throughout the cranial cavity, and particularly within those venous blood vessels lying within the subarachnoid and perivascular spaces. This effect is transmitted to and is reflected by the pressure of blood within the jugular vein in the neck. Since pressure within the jugular is related to the rate of flow of blood therein, a noninvasive technique may be utilized to detect the blood flow through that vein so as to yield determinable information concerning the intracranial pressure of the cerebrospinal fluid.

It has been discovered that the effects of the intracranial pressure on the jugular pressure are most readily determined during a relatively short interval of time following total occlusion of the jugular so as to cause an interruption in the flow of blood through the vein. During that short interval (on the order of five seconds) the blood flow approaches zero and the blood pressure increases markedly at a rate of change which varies with the intracranial pressure. Accordingly, a measurement of the change in jugular pressure or flow with time following occlusion will provide an accurate indication of the intracranial pressure during that same time interval.

Blood flow may be measured noninvasively by inducing and detecting a transcutaneous electrical impulse representative of blood flow within the jugular vein. This may be accomplished through the placement of suitable transducer electrodes on the surface of the skin of the neck of a patient on opposite sides of the jugular vein. A narrow width magnetic flux of low intensity is then passed through the vein between the electrodes at a direction perpendicular to the flow of blood to induce an electrical impulse to appear at the surface of the skin to be detected by the transducer electrodes. Following occlusion of the jugular vein at a point downstream of electrodes, the resulting electrical signals (representative of the rate of change of flow as the flow approaches zero) are transmitted to a receiving and control circuit by which they are filtered, amplified and manipulated or processed computationally to a value representative of the intracranial pressure. The resulting value of intracranial pressure may be displayed digitally or otherwise as desired for easy reference by an attending physician or other medical personnel.

BRIEF DESCRIPTION OF THE DRAWINGS

For a further understanding of the present invention, reference may be had to the accompanying drawings in which.

BRIEF DESCRIPTION OF THE PREFERRED EMBODIMENT

Figure 1:
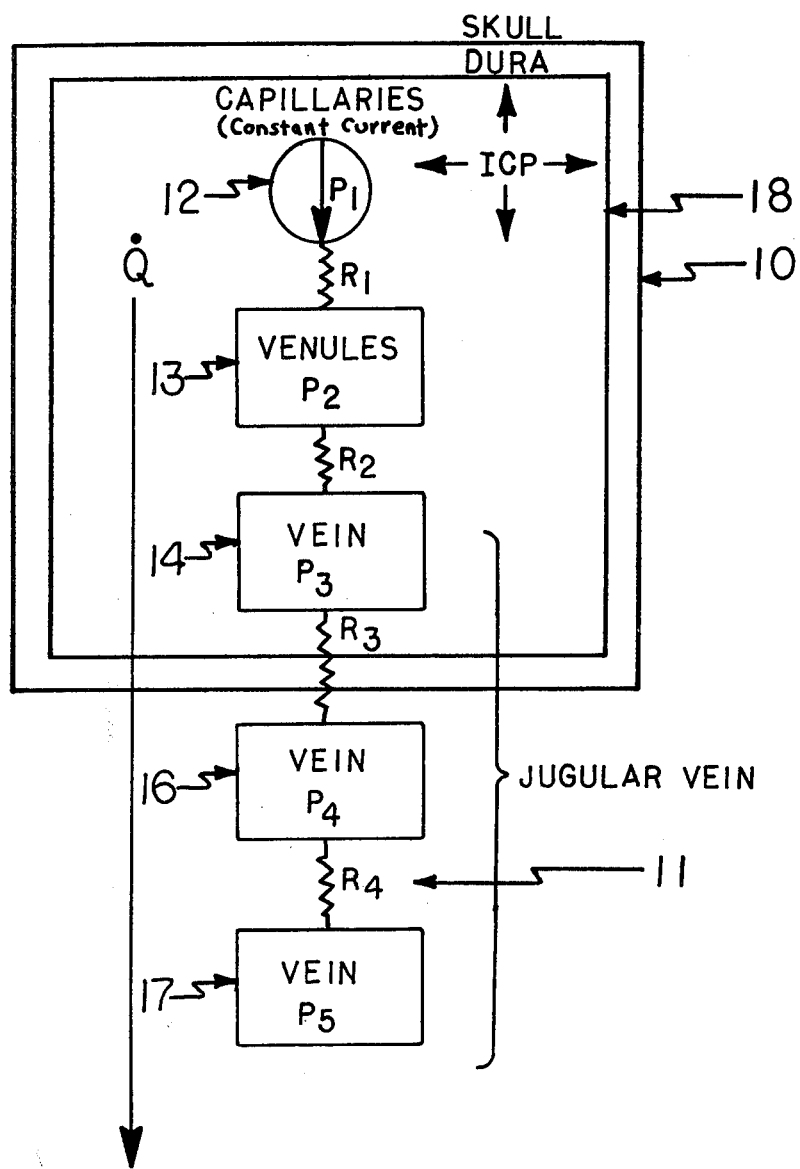
FIG. 1 is a schematic representation of the skull, dura and venous network therein of, for example, a mammal, including a portion of the jugular vein both inside and outside of the cranium.

Referring now to the drawings, and in particular to FIG. 1, there is illustrated a schematic diagram of a theoretical model of the intracranial venous system situated, for example, within and immediately external to the skull, represented in schematic form by a block 10, of a mammal, and in particular, a human being. The venous system also includes a portion, generally indicated by reference numeral 11, of the jugular vein located outside the head, generally in the neck of the individual. The several blood vessel networks of the head are also represented schematically in block form and, for convenience, the flow resistance of the vessels is represented by symbols generally utilized to illustrate electrical resistance.

The blood vessel network principally affected by the intracranial pressure to be measured by the present invention consists of a capillary network 12 having a pressure $P_1$ and resistance $R_1$ in fluid flow communication with venules 13 having pressure $P_2$ and resistance $R_2$. The venules 13 expand into a portion 14 of the jugular vein within the head, having pressure $P_3$ and resistance $R_3$, which extends outside of the skull to form the jugular vein in the neck of the individual, sections of which are indicated schematically by blocks 16 and 17. The capillaries, venules and jugular vein portion 14 are situated within the dura 18, a membrane which lies beneath the skull and above the subarachnoid space of the brain. The cerebrospinal fluid which exerts the pressure to be measured in accordance with the present invention (i.e., the intracranial pressure or ICP) is retained within the dura. As will be demonstrated below, the ICP acts upon the several venous networks of the brain in such a way as to induce a detectable disturbance in the pressure or flow of blood through the jugular vein 11.

The relationship between the ICP and the pressure $P_4$, for example in the jugular vein section 16, can be illustrated mathematically from the anatomical model depicted in FIG. 1. It is generally true that the rate of flow of a viscous fluid through a tube is directly proportional to the pressure difference between the ends of the tubes and inversely proportional to the resistance to fluid flow within the tube. Of course, resistance in this context is a complex concept and is defined or determined in part by the radius of the tube and the viscosity of the fluid. However, for present purposes, the relationship can be simply expressed as follows:

$$\dot{Q}=(\Delta P/R)$$

where $\dot{Q}$ is the flow, $\Delta P$ is the pressure differential and $R$ is the resistance.

With reference to FIG. 1, where the fluid is blood and the tube consists of the various blood vessel networks 12, 13, 14, 16 and 17, a series of relationships representative of the blood flow $\dot{Q}$ of the system can be derived as follows, assuming that the blood pressure for each blood vessel network within the dura 18 is affected by an ICP component:

$$\dot{Q} = \frac{(P_2 + ICP) - (P_1 + ICP)}{R_1} = \frac{P_2 - P_1}{R_1} \quad (a)$$

$$\dot{Q} = \frac{(P_3 + ICP) - (P_2 + ICP)}{R_2} = \frac{P_3 - P_2}{R_2} \quad (b)$$

$$\dot{Q} = \frac{P_4 - (P_3 + ICP)}{R_3} \quad (c)$$

$$\dot{Q} = \frac{P_5 - P_4}{R_4} \quad (d)$$

If it is now assumed that the blood flow Q for the entire venous system is interrupted so as to approach zero, then it follows from equations (a) through (c) that:

$P_2 = P_1$
$P_3 = P_2$
and $$P_4 = P_3 + ICP = P_1 + ICP \quad (e)$$

Accordingly, while the blood flow $\dot{Q}$ is zero, the pressures $P_1$, $P_2$ and $P_3$ within the dura are equal and constant so that from equation (e) it is seen that $P_4$ is directly proportional to the ICP. As the blood flow approaches zero then, a measurement of $P_4$ outside the skull of the patient will yield information which can be correlated with the ICP within the skull.

It will be seen from equation (d) above that one way to establish a zero flow rate within the venous system from outside the skull is to set $R_4$ at infinity. This may be achieved, for example, by temporarily occluding the jugular vein to prevent the blood from flowing through it. For a brief period of time following such occlusion, the jugular pressure $P_4$ will be directly proportional to the ICP as described above, so as to define a direct measure of the ICP.

By way of example, it has been established experimentally that for mammals, the rate of change of the jugular blood pressure with time following occlusion of the vein outside of but proximate to the brain cavity is directly proportional to the peak intracranial pressure of the cerebrospinal fluid, i.e., the higher the peak value of the ICP, the greater is the rate of change of jugular pressure. Thus a measure of the latter at any particular point in time may be calibrated to yield a corresponding value for the ICP.

Figure 2:
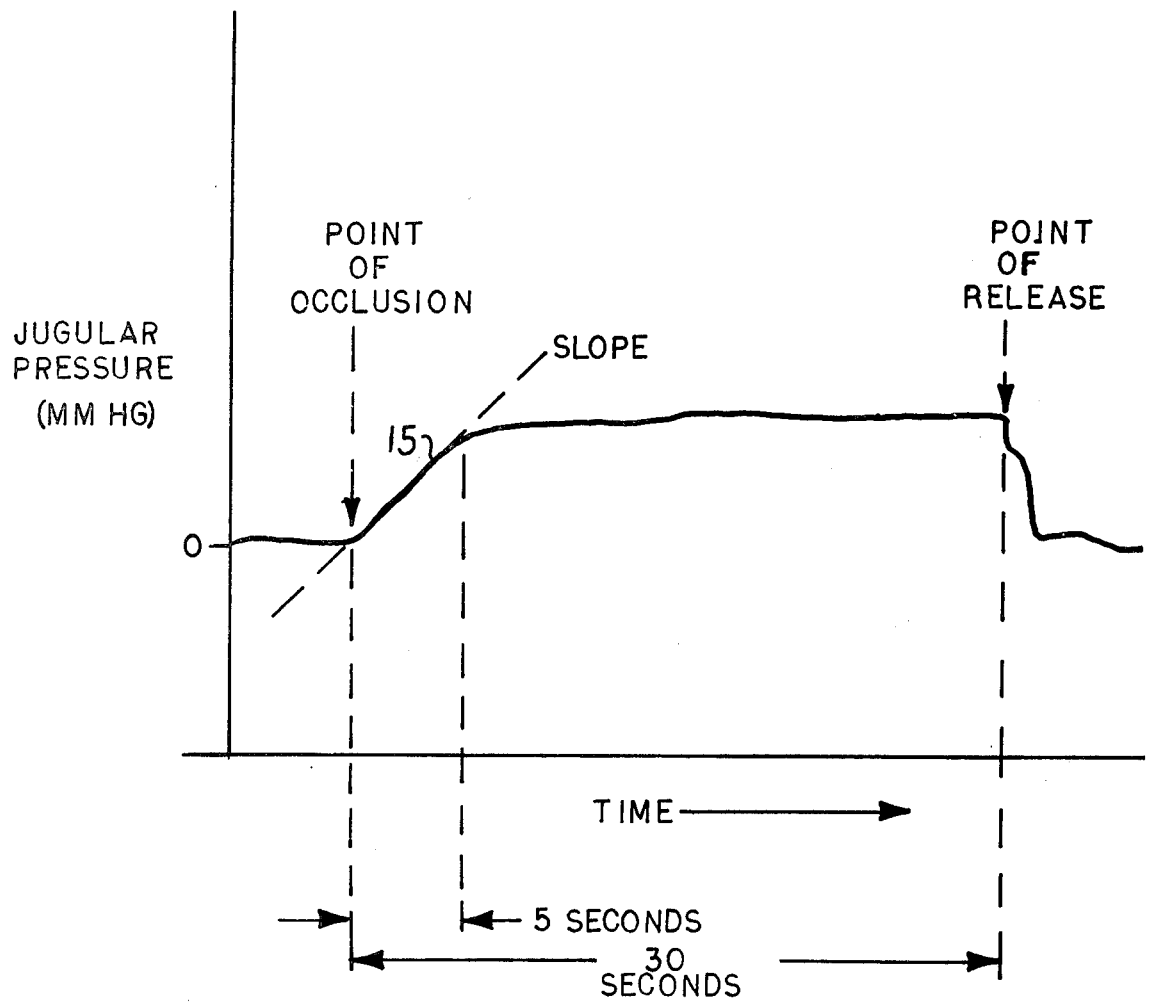
FIG. 2 is a graphic representation of the change in jugular pressure with time of a cat, the intracranial pressure of which was gradually raised artificially in the course of a laboratory experiment.
Figure 3:
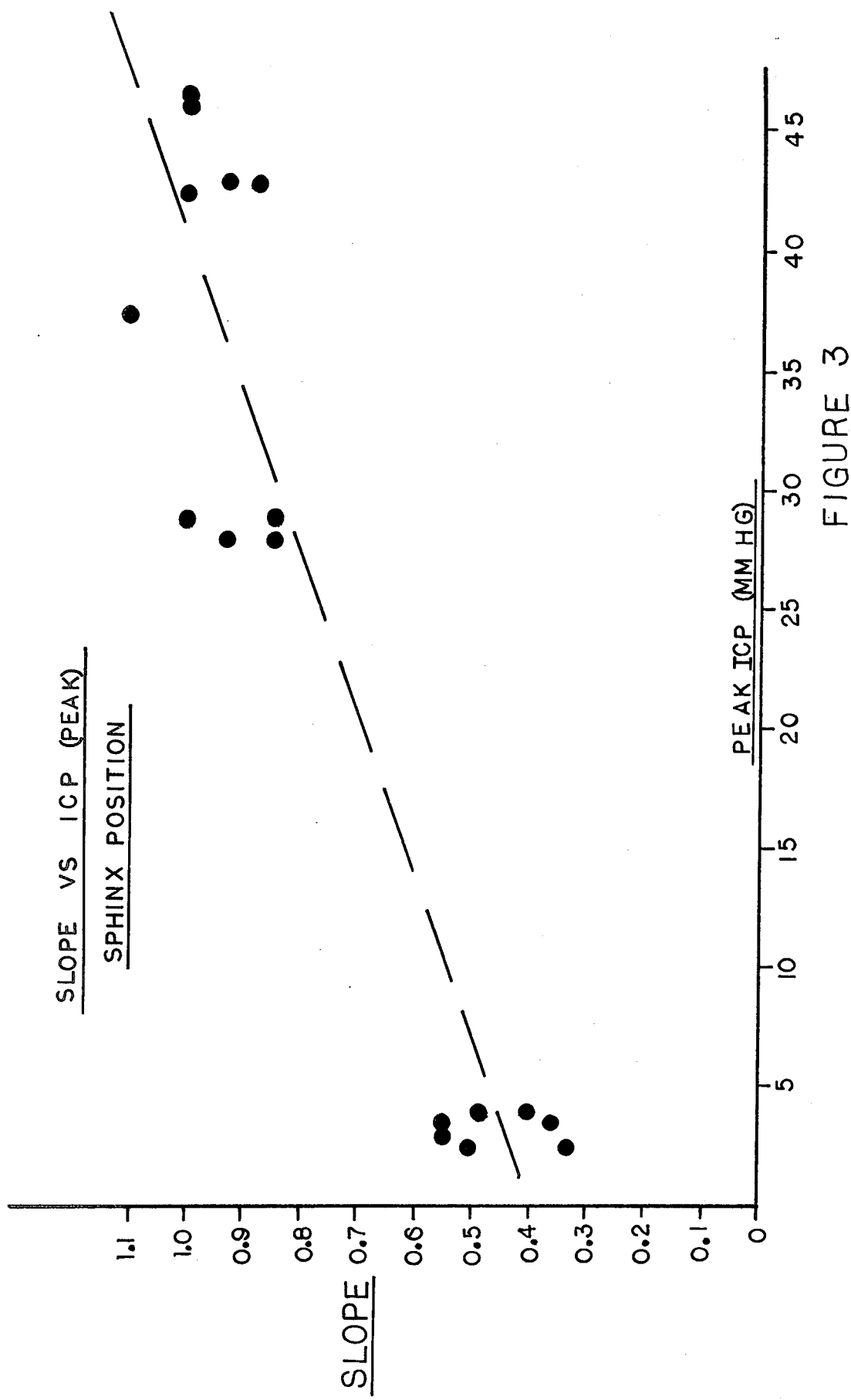
FIG. 3 is a graphic representation of experimental data which reflects the change in jugular pressure with time (or slope) versus the intracranial pressure of the cat, in the experiment reflected in FIG. 2.

The foregoing relationship is illustrated in the graphs of FIGS. 2 and 3 which have been generated on the basis of information derived from the following experiment:

A male cat was suitably prepared for a surgical procedure by the administration intramuscularly of approximately 3 cc of nembutal (anaesthesia) and the insertion of an endotracheal tube. Catheters were then surgically implanted in the femoral artery (to measure blood pressure), the femoral vein (to administer anaesthesia) and in the upper branch of the external jugular vein to permit accurate measurements of blood pressure to be taken. A catheter connected to standard pressure transducers was also placed in the cat's cisterna magna to enable measurement of ICP, a record of which was kept by a standard strip chart recorder. Peak and peak to peak ICP was determined by graphicalanalysis from the recorded data following the experiment. Measurements of the normal ICP were taken for the cat in both the sphinx and flat abdominal positions. In addition, continuous measurement of the jugular blood pressure throughout the experiment (both before and after occlusion of the vein) were made, and the normal peak-to-peak, peak ICP and jugular pressures were determined and recorded for each position. Thereafter, an infusion of saline solution into the cisterna magna at the rate of 0.369 cc/min were begun to raise artificially the ICP pressure. Continuous measurements of ICP and jugular pressure before and after occlusion were made and recorded for each infusion of saline solution. The net change in jugular pressure resulting from the occlusion, and the rate of change (or slope of the curve) of the jugular pressure with time following occlusion were also determined and recorded for each increase in ICP. These experimental results are set forth in tabular form in Table I which, excepte for the column headed "Slope," represents directly measured values, as follows:

TABLE I

| | Position | Peak ICP | Jug. Pres. Bef. Occl. | Jug. Pres. Aft. Occl. | $\Delta P_J$ | Slope (V/H) | P-P ICP | P-P Jug. Pres. |
|---|---|---|---|---|---|---|---|---|
| A | Sphinx | 3.5 | −13 | +8 | 21 | | 2 | 0 |
| B | Sphinx | 3.5 | −2 | +8 | 10 | .35 | 2 | 0 |
| C | Sphinx | 2.5 | −3 | +6 | 9 | .33 | 2 | 0 |
| D | Sphinx | 4.0 | 0 | +10 | 10 | .40 | 2 | 0 |
| E | Sphinx | 4.0 | 0 | 10 | 10 | .48 | 2 | 0 |
| F | Abdominal | 6.5 | 0 | 12 | 12 | | 1.5 | 2.5 |
| G | Abdominal | 6.0 | 0 | 12 | 12 | | 1.5 | 2.5 |
| H | Abdominal | 5.8 | 0 | 12 | 12 | | 1.5 | 2.5 |
| I | Sphinx | 2.8 | −4.5 | 10 | 14.5 | .55 | 2 | 0 |
| J | Sphinx | 2.5 | −4.5 | 10 | 14.5 | .50 | 2 | 0 |
| K | Sphinx | 3.5 | −2.5 | 11 | 13.5 | .55 | 2 | 0 |
| L | Sphinx | 29 | −2.5 | 19 | 21.5 | 1.0 | 4 | 0 |
| M | Sphinx | 29 | −3 | 19 | 22 | .83 | 6 | 0 |
| N | Sphinx | 28 | −4 | 17 | 21 | .83 | 3 | 0 |
| O | Abdominal | 29 | +2 | 22 | 20 | | 3.5 | 4 |
| P | Abdominal | 29.5 | +3 | 23 | 20 | | 3 | 4 |
| Q | Abdominal | 30 | +3 | 25 | 22 | | 4 | 5 |
| R | Sphinx | 28 | −3 | 20 | 23 | .93 | 3 | 0 |
| S | Sphinx | 37.5 | −4 | 20 | 16 | 1.1 | 4.5 | 2 |
| T | Sphinx | 47 | −2.5 | 21 | 18.5 | 1.0 | 3 | 2 |
| U | Sphinx | 48 | −2.5 | 21 | 18.5 | 1.0 | 3.5 | 2.5 |
| V | Sphinx | 42.5 | −3 | 20 | 23 | 1.0 | 3 | 2.5 |
| W | Abdominal | 45.5 | +2.5 | 24 | 21.5 | | 5 | 5.5 |
| X | Abdominal | 44 | +2.5 | 24 | 21.5 | | 5 | 5.5 |
| Y | Abdominal | 42 | +2.5 | 23 | 20.5 | | 5 | 5.5 |
| Z | Sphinx | 43 | −3 | 19 | 22 | .87 | 4.5 | 1.5 |

TABLE I-continued

| | Position | Peak ICP | Jug. Pres. Bef. Occl. | Jug. Pres. Aft. Occl. | $\Delta P_J$ | Slope (V/H) | P-P ICP | P-P Jug. Pres. |
|---|---|---|---|---|---|---|---|---|
| AA | Sphinx | 43 | −3.5 | 19 | 22.5 | .93 | 4.5 | 1.5 |

For each measurement represented in Table I, a conventional strip chart record was kept continuously showing graphically, among other things, the value of the jugular blood pressure as it varied with time, both before and after the point of jugular occlusion. A representative graph of the relationship of jugular pressure and time is depicted in FIG. 2.

As shown in FIG. 2, the jugular pressure rises steeply (i.e., the curve defines a ramp portion 15) for a period of about 5 seconds immediately following occlusion and then begins to level off. This corresponds inversely to the rate of change of blood flow in the vein as it approaches zero. For experimental purposes, the jugular occlusion in the experiment reflected in Table I was retained for a total of 30 seconds, a period of time which, while not believed to be dangerous to the animal, is somewhat lengthy for use of the present technique on human beings. It will be observed however that following the initial rapid rise in jugular pressure during the first 5 seconds of occlusion, the curve remains substantially level for the next 25 seconds until the occlusion is released. Accordingly, the desirable ICP information will be derived from the ramp portion 15 of the curve of FIG. 3 during approximately the first 5 seconds following occlusion of the jugular. A procedure involving measurements to be made over an interval of such short duration will not cause any discomfort or danger to the patient.

As demonstrated by the data derived from the foregoing experiment and set forth in Table I, there is a determinable relationship, depicted in FIG. 3, between the rate of change of external jugular pressure with time following occlusion (i.e. the slope of the ramp portion 15 of the curve of FIG. 2) and the ICP. It is clear that as the ICP is increased, the value of the slope of the ramp portion of FIG. 2 also increases. The plot of data represented in FIG. 3 therefore serves to verify the assumption made in connection with the mathematical model derived from FIG. 1. Of course additional routine experimentation would be desirable from a scientific point of view in order to calibrate, for purposes of instrumentation, the pressure information plotted in FIG. 3 and the actual value of the ICP at any particular point in time. The foregoing experiment however demonstrates the soundness and accuracy of the heretofore unrealized effect of ICP on jugular pressure for mammals.

Of course the data of Table I may be shown to demonstrate other relationships between ICP and jugular pressure. For example, a graph showing a correlation similar to that represented in FIG. 3 results from plotting the peak ICP against the net change in jugular pressure ($\Delta P_J$) following occlusion. Moreover, the data demonstrates a nearly one to one correlation between the peak-to-peak ICP and the peak-to-peak jugular pressure regardless of whether the jugular is occluded. Since there is believed to be a correlation between peak to peak ICP and peak ICP, a direct measurement of the peak to peak jugular pressure should provide information which can be correlated to peak ICP. As the foregoing experiment demonstrates, however, an accurate and easily determinable measure of ICP can be obtained through the technique of occluding the jugular and determining the rate of change of jugular pressure with time during approximately the first 5 seconds following occlusion, as set forth above.

Although the foregoing data was derived invasively from a mammal through standard catheter techniques, similar data can be derived noninvasively. Since the change of blood pressure with time following occlusion of the jugular vein corresponds to the change of blood flow rate within the vein, certain noninvasive techniques described below may be utilized to obtain a measurement of the rate of change of flow as it approaches zero as a result of the occlusion. Thus, for the present invention, ICP information may be derived with equal accuracy and reliability by monitoring either the blood pressure or the blood flow following temporary occlusion of the jugular vein, although the latter is preferred.

Figure 4:
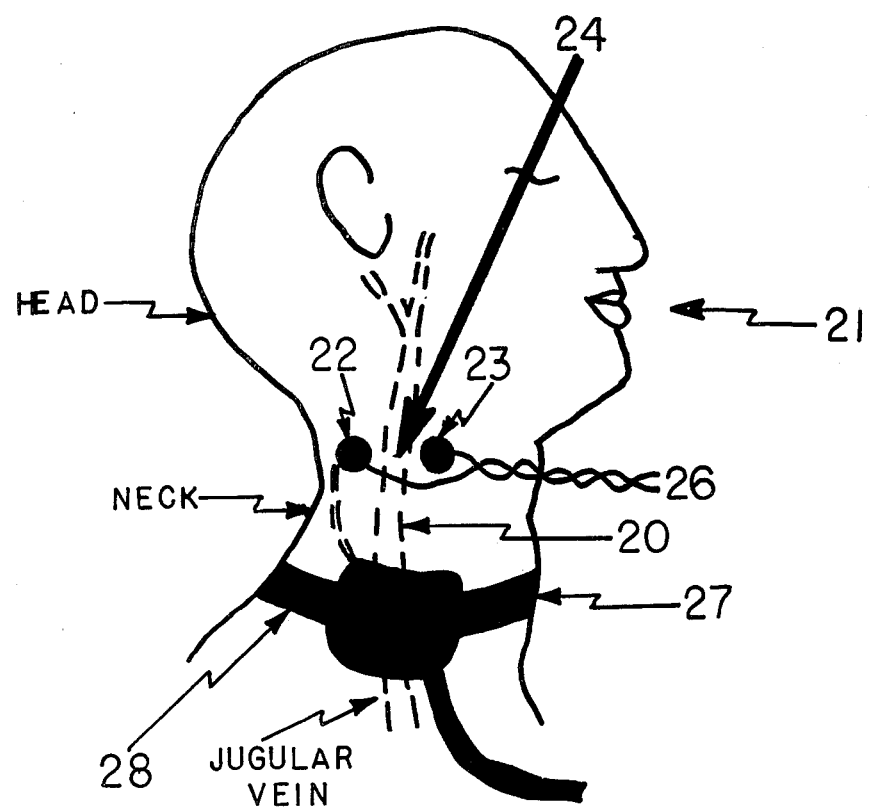
FIG. 4 is an anatomical representation of a human head and neck showing the jugular vein and the placement of electrodes for deriving magnetically induced blood flow information in accordance with the present invention.

Referring now to FIG. 4, there is illustrated a type of blood flow monitor which may be employed to register blood flow in a vessel of a living being without the necessity of surgical implantation of catheters and the like. By way of example, the noninvasive technique is shown in connection with measuring the blood flow in the right jugular 20 in the neck of a patient 21. A pair of suitable transducer electrodes 22 and 23 is placed on the neck of the patient on opposite sides of the jugular vein 20. A small electromagnet, represented schematically and illustrated by reference numeral 24, is placed over the jugular vein between the electrodes 22 and 23. For present purposes, the electromagnet is connected to a standard d.c. power supply (not shown) which is preferably driven by a conventional 400 Hz square wave oscillator (not shown).

The electromagnet is designed so as to produce a narrow width of low intensity magnetic flux and is oriented so that the flux field is perpendicular to both the jugular vein and the direction of blood flow within the vein. Of course, the strength of the magnetic field is such that a detectable electrical signal induced by the passage of blood through the magnetic field crossing through the jugular vein will be present at the surface of the skin in the vicinity of the electrodes. The electromagnet may be affixed to a suitable transport mechanism (not shown) which will facilitate proper positioning and retention of the magnet over the skin and jugular vein between the electrodes. The electrical signal produced at the skin by the flow of blood through the magnetic field is detected by the electrodes and is carried by a suitably shielded and twisted wire pair 26 to an electronic measurement and control system described in detail below.

Figure 5:
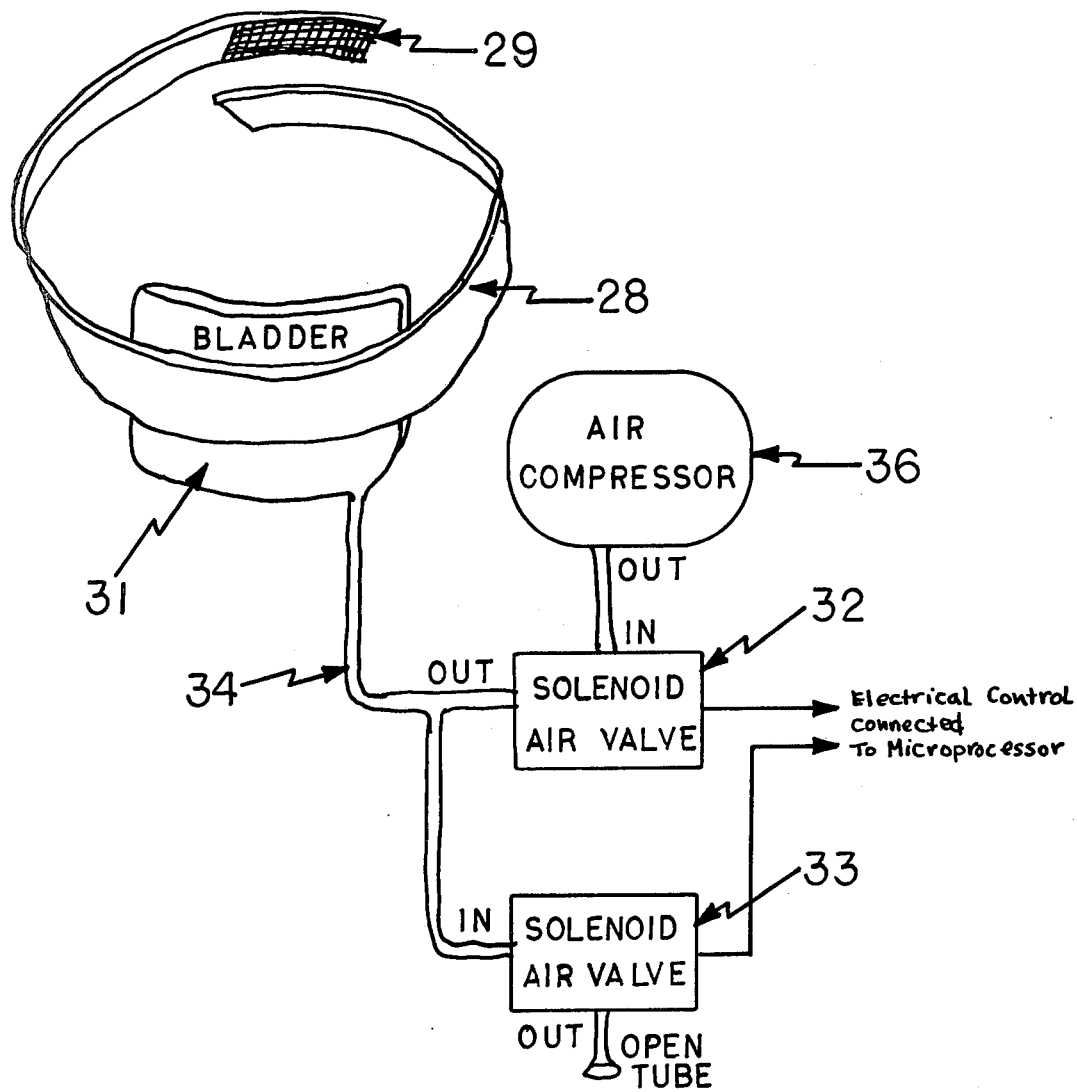
FIG. 5 is a perspective view of an implement for occluding the jugular vein and includes a block diagram of a pneumatic system for controlling the implement.

Occlusion of the jugular vein at a point downstream of the emplacement of the electrodes 22 and 23 may be accomplished manually or by the use of an automatic occlusion device 27 attached around the neck of the patient. With reference to FIGS. 4 and 5, the automatic occluder consists of a suitable strap 28 which may be lightly secured around the patient's neck by means of a velcro friction lock 29, or the like. An expandable bladder 31 of predetermined size is affixed to the strap 28 and is adjusted to engage the surface of the neck at a point directly overlying the jugular vein. The bladder 31 is in fluid flow communication with a pair of controlling solenoid air valves 32 and 33 through a suitably flexible and preferably vinyl tube 34. One of the solenoid valves, for example, the valve 32, is operably connected to a source 36 of compressed air such as a conventional air compressor. The valve 32 acts selectively to permit the bladder 31 to be inflated so as to perform the occlusion of the jugular vein as desired. The other valve 33 serves selectively to vent the bladder to release the pressure on the neck following the occlusion procedure. Both valves are connected to and are controlled by the measurement and control system described below.

Figure 6:
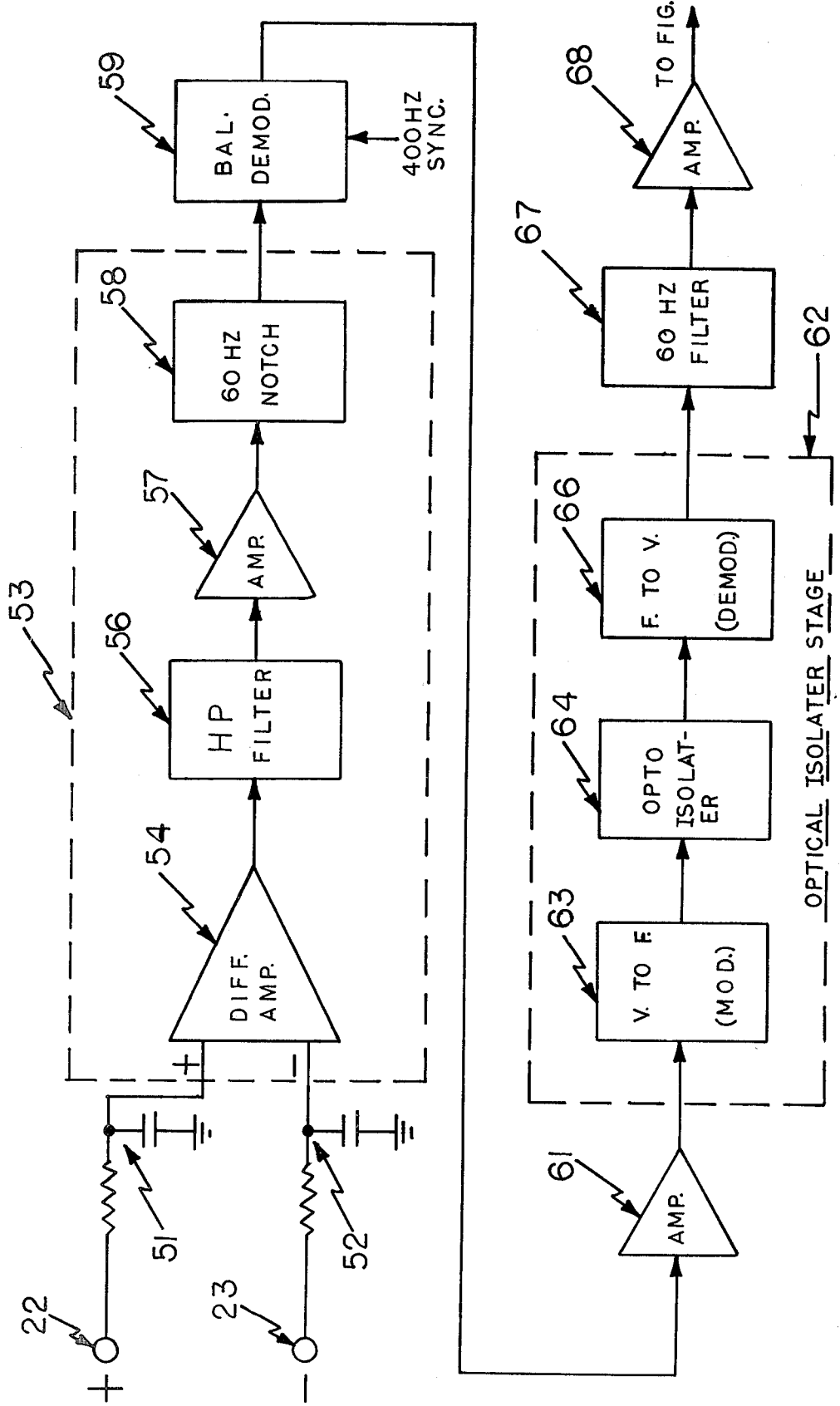
FIG. 6 is a block diagram of one embodiment of an analog signal amplification and preparation system for acting upon the signal derived by the electrodes shown in FIG. 4.

Referring now to FIG. 6, there is illustrated one embodiment in simplified block form of a portion of a measurement and control system consisting of suitable electronic circuitry for processing the low level 400 Hz modulated input signal, provided by electrodes 22 and 23. As will be discussed below, this circuitry is also adapted to isolate the patient from the power sources of the system, thereby protecting the patient from electric shock in the event of any malfunction in the system.

The signals transmitted by electrodes 22 and 23 are each passed through a corresponding one of a pair of identical 500 KHz filters 51 and 52, thereby to eliminate any radio frequency interference from the signals. From these filters, the signals are presented to a first amplification and filtering stage 53, which preferably consists of a differential amplifier 54, a high pass filter 56, an amplifier 57, and a 60-Hz notch filter 58.

The differential amplifier 54 is of conventional low noise design and has the characteristics of high input impedance, high common-mode rejection, and low input bias current. The common mode rejection characteristic of the amplifier 54 serves to eliminate any common mode 60-Hz signals appearing at its inputs. In its preferred embodiment, the differential amplifier 54 includes conventional 2000 Hz filtering for eliminating harmonics of the 400-Hz input signals and other spurious high frequency signals.

The high pass filter 56 is preferably arranged to have a time constant of 0.1 seconds and, therefore, eliminates spurious signals below 10 Hz which could be caused, for example, by the patient's electrocardiogram. The 60-Hz notch filter 58 consists of a passive network of resistors and capacitors arranged in conventional form to provide further rejection of extraneous 60-Hz signals, which may not have been previously eliminated by the common mode rejection characteristics of the differential amplifier.

After the processed signal leaves the amplification and filtering stage 53, the 400-Hz carrier component of the signal is eliminated by a balanced demodulator 59. A Motorola MC 1596G balanced demodulator, for example, may be used for this purpose. Synchronization for this demodulator may be provided by a signal path to the 400-Hz square wave oscillator (not shown) which is used to drive the electromagnet 24 (FIG. 4). The output of the demodulator 59 is an analog signal corresponding to the velocity of blood flow in the patient's jugular vein. This signal is further amplified by an amplifier 61 which may also include additional 2000 Hz filtering as desired.

The output of the amplifier 61 is presented to the input side of an optical isolation stage 62 which serves to isolate the patient from electrical attachment to any of the succeeding stages of the apparatus thereby to protect the patient from electrical shock in the event of a malfunction in the electrical equipment. The optical isolation stage 62 includes a voltage-to-frequency converter (modulator) 63, an opto-isolator 64, and a frequency-to-voltage converter (demodulator) 66. In the present embodiment, the modulator 63 may be a Datel Model VFV-100K which modulates the signal provided by amplifier 61 with a 100 KHz carrier signal. The bandwidth is preferably set at 300 Hz. The Opto-isolator 64 may be, for example, a Hewlett-Packard Model 6N139 which converts the 100 Hz modulated signal from the modulator 63 into corresponding light pulses by means of a light-emitting diode. These light pulses are then converted back to corresponding electrical signals by means of a light-sensing diode. Thus, complete electrical isolation is provided between the input terminal and output terminal of the optical isolator 64. The 100 KHz signal from the output of the opto-isolator 64 is fed to the demodulator 66 which for present purposes may be a Datel Model VFV-100K, with a carrier center frequency of 100 KHz and a bandwidth of 300 Hz. The Demodulator 66 serves to eliminate the 100 Hz carrier signal which was overlaid on the analog signal output of amplifier 61 by the modulator 63.

The resulting analog signal output of the demodulator 66 undergoes additional 60 Hz filtering by means of a 60 Hz filter 67. In the present embodiment the filter 67 is a multiple feedback low pass active filter with a gain of 1.5 and a notch depth of $-40$ db./decade at 60 Hz. After leaving filter 67 the analog signal undergoes an additional stage of amplification by means of a conventional voltage amplifier 68. The output from the voltage amplifier 68 is thereafter supplied to an analog to digital converter 71 and to a strip chart recorder 72 shown in FIG. 7.

It will be noted that power for the circuitry described above is preferably provided by a "super-isolated" power supply (not shown) such as the Stevens-Arnold Model PS-4130, which utilizes a 5 volt input, and provides outputs of ±15 volts at ±150 milliamps. The input-to-output isolation characteristic of this supply is $10^{11}$ Ohm, 5 picofarads, and 8000 volts d.c. The use of such a supply as described above, or its equivalent, is necessary to provide electrical isolation between the patient and the power sources of the system, without the use of batteries, thereby providing protection against accidental electrical shocks.

Figure 7:
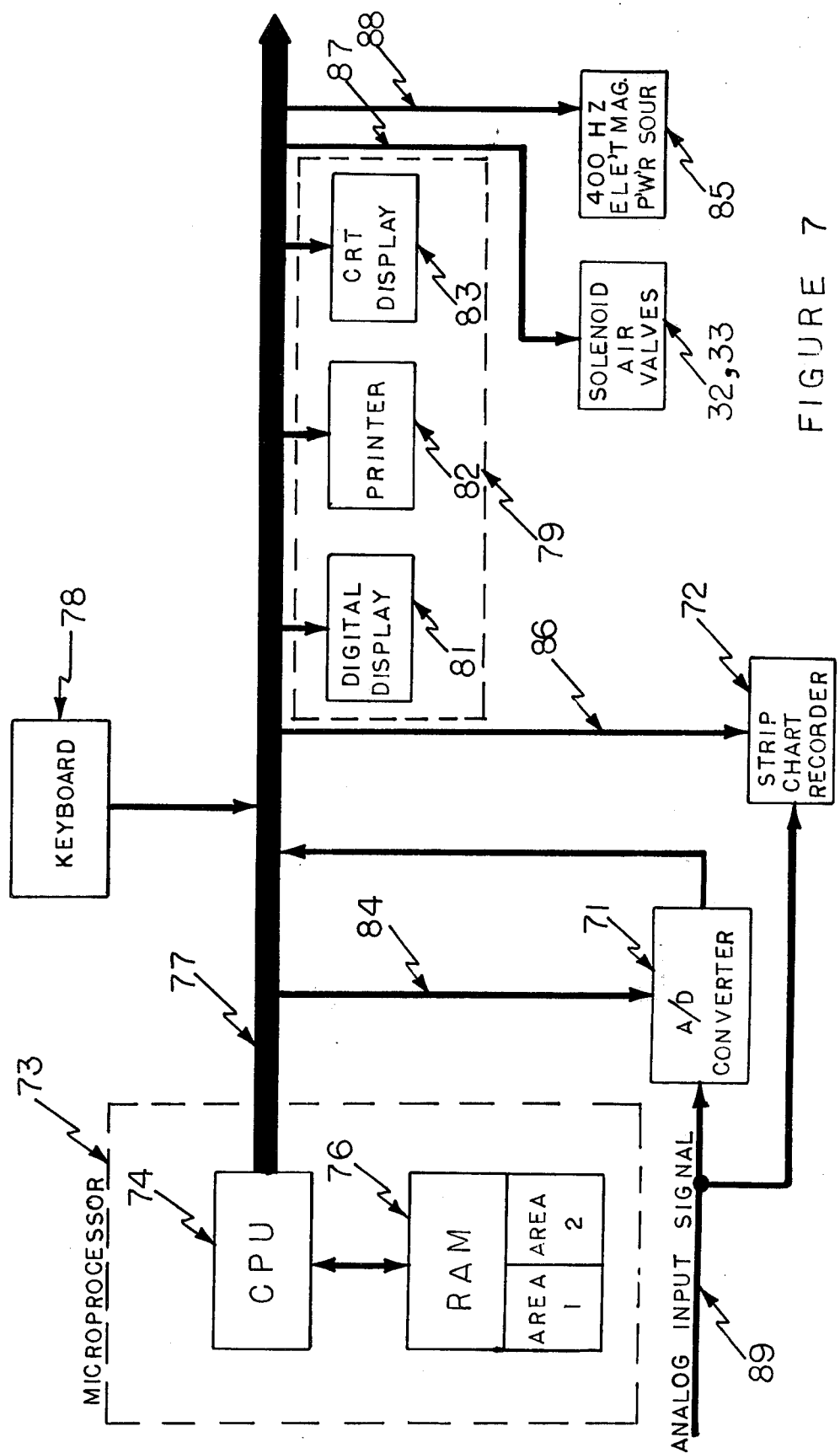
FIG. 7 is a block diagram of a microprocessor control system and peripheral devices for determining and displaying desired pressure information derived from the patient in accordance with the present invention.

With reference to FIG. 7, a conventional computer or microprocessor 73 may be used to provide various desirable control functions for the intracranial pressure monitoring process. The microprocessor 73 is preferably of the type which includes a CPU 74 and a random access memory 76 which may be thought of as being divided into several storage areas such as storage area 1 and storage area 2. The microprocessor 73 communicates with or controls the other units of the system by way of a plurality of signal paths included in a bus 77. These other units may include a keyboard input device 78, and a plurality of digital output devices, generally indicated by reference numeral 79, and which might include, for example, a digital display device 81, a printer 82, and a CRT display device 83. The microprocessor 73 is also adapted to control or synchronize the operations of the analog-to-digital converter 71, the strip chart recorder 72, the solenoid air valves 32 and 33 (FIG. 5), and the 400 Hz power source 85 for the electromagnet 24. Such control is exercised by way of a plurality of signal paths 84, 86, 87 and 88, respectively.

In a typical operation, the operator will first enter various process control and patient history data into the microprocessor 73 by way of the keyboard 78, for example. The patient history data may include, for example, the patient's name, age, time of day, and medical record number. This data will be stored in a first storage area of random access memory 76 for later retrieval and printout along with the measurement results. The control information may include information as to the length of each measurement, the elapsed time between measurements, whether an automatic occluder is to be utilized, and the rate at which the data provided by the analog-to-digital converter 71 is to be sampled during the measurements. All of the above control information is stored in the first storage area of random access memory 76 where it is available for reference by the various process control programs of the microprocessor.

After the above information is entered, and the electrodes 22 and 23 are positioned on the neck of the patient as shown in FIG. 4, the electromagnet 24 is moved into position above the jugular vein. The microprocessor 73 initiates the first measurement by activating the electromagnet power source 85 and turning on strip chart recorder 72. It then activates the appropriate one of solenoid air valves, for example air valve 32 (FIG. 5), for permitting air from the compressor 36 to inflate the bladder 31 of the automatic occluder, thereby to occlude the patient's jugular vein. At the same time a programmable timer for determining the length of the measurement is started. Typically, the duration of the measurement will be about 20 seconds.

After the measurement cycle is initiated, an analog signal 89 corresponding to the rate of blood flow in the patient's jugular vein is provided, following processing by the amplifier 68 (FIG. 6), to the strip chart recorder 72 and the analog-to-digital converter 71. The strip chart recorder 72 provides a hard copy record of this signal.

The analog-to-digital converter 71 converts the analog signal into digital data readable by the microprocessor 73. At a predetermined sampling rate (typically 10 milliseconds), the microprocessor samples the digital output of the analog-to-digital converter 71 and stores this data in the second storage area 2 of the random access memory 76. When the previously discussed programmable timer "times out," the microprocessor terminates the measurement cycle by turning off the chart recorder 72 and the power source 85. The release valve 33 is also activated so as to vent air from the bladder 31 to inactivate the automatic occluder. The microprocessor then processes data previously stored in the storage area 2 of the random access memory 76 to make predetermined calculations such as the peak value, peak to peak value and the slope of the blood flow wave form. As previously noted, these calculated values may be correlated to the patient's ICP. After performing the necessary calculations, the microprocessor causes the desired data, such as a digital read out of the computed ICP, to be displayed on the appropriate one or ones of the digital output devices 79. The measurement may be repeated as often as is necessary and at desired intervals depending on the patient's clinical symptoms, without requiring the patient to remain wired up to the device between measurements, depending on the period of time between measurements. Since surgical implantation is not required, a patient may have its ICP monitored at home, in a doctor's office or in an ambulance without danger of infection or electrical shock.

Various modifications will occur to those skilled in the pertinent art. Accordingly, the scope of the present invention is not to be limited except as defined by the following claims.

What is claimed is:

1. A method for obtaining from mammals a representation of the pressure of cerebrospinal fluid within the cranium, comprising the steps of:
    occluding the jugular vein at a selected location outside the cranium to interrupt the flow of blood therethrough; and
    determining a value corresponding to the rate of change of blood pressure within the jugular vein upstream of said location over a predetermined period of time following occlusion thereof.

2. The method of claim 1 in which said determining step comprises:
    deriving information representative of the flow of blood within the jugular continuously during said predetermined period of time following said occlusion; and
    calculating from said information a value representative of the rate of change of said blood flow during said predetermined period.

3. The method of claim 2 in which said deriving step comprises inducing an electrical signal representative of the flow of blood within the jugular, detecting said signal and recording said signal.

4. The method of claim 3 in which said electrical signal is induced by:
    placing a magnet adjacent the jugular vein upstream of said selected location such that the lines of magnetic flux traverse the vein in a direction perpendicular to the direction of blood flow within the vein, thereby to induce a transcutaneous electrical signal in the vicinity of the vein; and
    detecting said signal with a pair of spaced apart electrodes, one on each side of said vein and said magnet.

5. The method of claim 4 in which the magnet is an electromagnet, and said electrical signal is induced by energizing said magnet with power from an alternating current source having a frequency in the range of from above 60-Hz to approximately 2000 Hz.

6. The method of claim 1 in which said occluding step comprises placing an inflatable bladder over the jugular vein at said selected location, and inflating said bladder for at least said predetermined period of time to cause it to expand against and to constrict the jugular vein to interrupt blood flow therethrough.

7. The method of claim 1 in which the jugular vein is occluded for a period of time in the range of from 5 to 20 seconds.

8. The method of claim 7 in which the rate of change of blood flow within the jugular vein is determined over a period of approximately five seconds following said occlusion.

9. Apparatus for obtaining from mammals a representation of the pressure of cerebrospinal fluid with the cranium comprising:
    means for occluding the jugular vein at a selected location outside the cranium to interrupt the flow of blood therethrough, and
    means for determining a value corresponding to the rate of change of blood pressure within the jugular vein upstream of said location over a predetermined period of time following occlusion thereof.

10. The apparatus of claim 9 in which said determining means comprises means for inducing a transcutaneous electrical signal representative of the blood flow within the jugular vein; means for detecting said signal; means for converting said signal to machine readable data; and means for performing mathematical operations on said data.

11. The apparatus of claim 10 in which said signal inducing means comprises a magnet oriented with respect to the jugular vein such that the lines of flux traverse the vein substantially perpendicular to the direction of blood flow therein.

12. The apparatus of claim 11 in which said magnet comprises an electromagnet driven by an alternating current source having a frequency of $f_1$;

said signal thereby comprising an amplitude modulated signal having a frequency of $f_1$ and an envelope corresponding to the velocity of the flow of blood through the jugular vein.

13. The apparatus of claim 12 in which said signal detecting means comprises a pair of transducer electrodes adapted to be positioned on the surface of the skin, one on each side of the jugular vein and said magnet.

14. The apparatus of claim 13 in which said signal converting means comprises means operatively connected to said electrodes for amplifying and filtering said signal.

15. The apparatus of claim 14 in which said amplification and filtering means comprises:

means for eliminating from said signal signal components having frequencies substantially higher than $f_1$.

16. The apparatus of claim 15 in which said signal converting means further comprises:

means for demodulating said amplitude-modulated signal and for generating an analog signal having an amplitude corresponding to the envelope of said amplitude modulated signal;

an analog-to-digital converter connected to said amplification and filtering means for converting said analog signal into digital data; and a computer adapted to perform mathematical operations upon said digital data.

17. The apparatus of claim 16 in which said occluding means comprises an inflatable bladder to overlie the jugular vein; a source of air under pressure; and a pair of electrically operated valves in fluid flow communication with said bladder, one of which is connected to said source, said valves being selectively operable alternately to inflate and vent the bladder.

18. The apparatus of claim 17 in which said computer is electrically connected to said valves and is adapted selectively to activate said valves thereby to control inflation and deflation of said bladder.

19. The apparatus of claim 17 in which said computer is electrically connected to the source of current for said electromagnet thereby to control activation thereof synchronously with control of the operation of said valves.

20. The apparatus of claim 19 in which the lines of flux generated by said magnet are substantially localized to a region closely surrounding the jugular and said electrodes.

21. The apparatus of claim 20 in which $f_1$ is approximately 400 Hz.

* * * * *